United States Patent [19]

Bach et al.

[11] 4,282,362

[45] Aug. 4, 1981

[54] OCTAHYDRO-2H-PYRROLO[3,4-g]QUINO-LINES

[75] Inventors: Nicholas J. Bach; Edmund C. Kornfeld, both of Indianapolis, Ind.

[73] Assignee: Eli Lilly and Company, Indianapolis, Ind.

[21] Appl. No.: 141,750

[22] Filed: Apr. 18, 1980

Related U.S. Application Data

[60] Division of Ser. No. 31,642, Apr. 19, 1979, Pat. No. 4,235,909, which is a continuation-in-part of Ser. No. 5,062, Jan. 22, 1979, abandoned.

[51] Int. Cl.$^3$ ............................................ C07D 471/04
[52] U.S. Cl. ....................................... 546/84; 424/258

[58] Field of Search ......................................... 546/84

[56] References Cited

U.S. PATENT DOCUMENTS

| 3,891,652 | 6/1975 | Hauck et al. | 546/84 |
| 3,898,236 | 8/1975 | Hauck et al. | 546/84 |
| 3,901,897 | 8/1975 | Hauck et al. | 546/84 |

Primary Examiner—Alan L. Rotman
Attorney, Agent, or Firm—James L. Rowe; Arthur R. Whale

[57] ABSTRACT

Octahydro-2H-pyrrolo[3,4-g]quinolines, useful as dopamine agonists, particularly as inhibitors of prolactin secretion and in treatment of Parkinsonism.

4 Claims, No Drawings

OCTAHYDRO-2H-PYRROLO[3,4-g]QUINOLINES

This is a division of application Ser. No. 31,642, now U.S. Pat. No. 4,235,909, filed Apr. 19, 1979, which was a continuation-in-part of our application Ser. No. 5,062 filed Jan. 22, 1979, now abandoned.

DESCRIPTION OF THE INVENTION

This invention provides trans-dl-5 and 7-substituted-4,4a,5,6,7,8,8a,9-octahydro-2H-pyrrolo[3,4-g]quinolines of the following structure

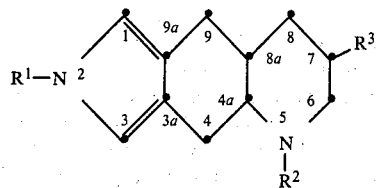

wherein $R^1$ is H, $(C_1-C_3)$alkyl-CO or $C_1-C_3$ alkyl; $R^2$ is H, $C_1-C_3$ alkyl, allyl or benzyl and $R^3$ is H, COO($C_1-C_3$) alkyl, COOH or $CH_2X$ wherein X is OH, Cl, Br, $OSO_2(C_1-C_3)$alkyl, $OSO_2$tolyl, $OSO_2$phenyl, CN, $CONH_2$, $SO_2CH_3$, $SCH_3$ or $OCH_3$, and acid addition salts thereof, preferably pharmaceutically-acceptable acid addition salts thereof formed with non-toxic acids.

In the above formula, the ring junction (the 4a, 8a bond) is trans and the compounds are obtained as a racemic pair. The two stereoisomers constituting the racemate can be drawn as structures Ia and Ib below

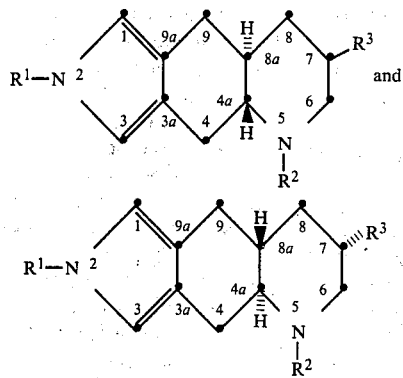

In addition, introduction of a substituent at C-7 ($R^3$ is other than H) creates a new chiral center and the compounds of that structure exist as 4 stereoisomers in two racemic pairs. The synthetic procedures to be set forth herein yield a single predominant racemate consisting of the 4aβ,7β,8aα isomer and its mirror image, the 4aα,-7α,8aβ isomer. Resolution of this racemate into its component diastereoisomers can be readily accomplished by methods currently available in the art. Regardless of the structure currently assigned to a given isomer or racemate, this invention provides compounds of the above formula having dopaminergic activity, whether in pure form as a single diastereoisomer or admixed with one, or more, less active or even inactive diastereoisomers.

Compounds according to Formula I above in which $R^2$ is $C_1-C_3$ alkyl or allyl, $R^1$ is H or $(C_1-C_3)$alkyl and $R^3$ is H or $CH_2X$ wherein X is $SCH_3$, $OCH_3$, $SO_2CH_3$, CN or $CONH_2$ and the pharmaceutically-acceptable acid addition salts thereof are useful as dopamine agonists, as will be set forth more fully below. Those compounds according to Formula I in which $R^1$ is lower alkanoyl or $R^2$ is H or benzyl or $R^3$ is COO($C_1-C_3$)alkyl, COOH, or $CH_2X$ wherein X is OH, Cl, Br, $OSO_2(C_1-C_3)$alkyl, $OSO_2$tolyl or $OSO_2$phenyl, and acid addition salts thereof, though having some dopamine agonist activity, are chiefly useful as intermediates.

In the above formulas, the term "$C_1-C_3$ alkyl" includes methyl, ethyl, n-propyl and isopropyl.

The pharmaceutically-acceptable acid addition salts of this invention include salts derived from inorganic acids such as: hydrochloric acid, nitric acid, phosphoric acid, sulfuric acid, hydrobromic acid, hydriodic acid, nitrous acid, phosphoric acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

The intermediates coming within the scope of Formula I form useful salts with all varieties of acids, not just non-toxic acids, and these salts are used for reaction and purification purposes.

Illustrative compounds falling within the scope of this invention include:
trans-dl-2,5-dimethyl-7-methylmercaptomethyl-4,4a,5,6,7,8,8a,9-octahydro-2H-pyrrolo[3,4-g]quinoline sulfate
trans-dl-4,4a,5,6,7,8,8a,9-octahydro-2H-pyrrolo[3,4-g]quinoline sulfate
trans-dl-2-methyl-7-methoxymethyl-4,4a,5,6,7,8,8a,9-octahydro-2H-pyrrolo[3,4-g]quinoline sulfate
trans-dl-5-methyl-4,4a,5,6,7,8,8a,9-octahydro-2H-pyrrolo[3,4-g]quinoline hydrochloride
trans-dl-2-acetyl-5-ethyl-7-cyanomethyl-4,4a,5,6,7,8,8a,9-octahydro-2H-pyrrolo[3,4-g]quinoline tartrate
trans-dl-2-n-propionyl-5-n-propyl-4,4a,5,6,7,8,8a,9-octahydro-2H-pyrrolo[3,4-g]quinoline fumarate
trans-dl-5-isopropyl-4,4a,5,6,7,8,8a,9-octahydro-2H-pyrrolo[3,4-g]quinoline
trans-dl-2-n-butyryl-5-benzyl-7-methoxycarbonyl-4,4a,5,6,7,8,8a,9-octahydro-2H-pyrrolo[3,4-g]quinoline
trans-dl-2-isobutyryl-7-hydroxymethyl-4,4a,5,6,7,8,8a,9-octahydro-2H-pyrrolo[3,4-g]quinoline
trans-dl-2-methyl-5-n-propyl-7-methylsulfonylmethyl-4,4a,5,6,7,8,8a,9-octahydro-2H-pyrrolo[3,4-g]quinoline maleate
trans-dl-5-ethyl-4,4a,5,6,7,8,8a,9-octahydro-2H-pyrrolo[3,4-g]quinoline trans-dl-5-allyl-4,4a,5,6,7,8,8a,9-octahydro-2H-pyrrolo[3,4-g]quinoline trans-dl-5-methyl-7-mesyloxymethyl-4,4a,5,6,7,8,8a,9-octahydro-2H-pyrrolo[3,4-g]quinoline trans-dl-2-ethyl-4,4a,5,6,7,8,8a,9-octahydro-2H-pyrrolo[3,4-g]quinoline trans-dl-2,5-dimethyl-7-p-tosyloxymethyl-4,4a,5,6,7,8,8a,9-octahydro-2H-phrrolo[3,4-g]quinoline.

The compounds of this invention in which $R^3$ is H are prepared according to the procedure outlined in Reaction Scheme I below. In Reaction Scheme I, only one stereoisomer has been drawn for convenience, but it should be remembered that each decahydroquinoline and each octahydropyrrolo[3,4-g]quinoline exists as a racemate. In addition, $R^2$ is other than H.

Reaction Scheme I

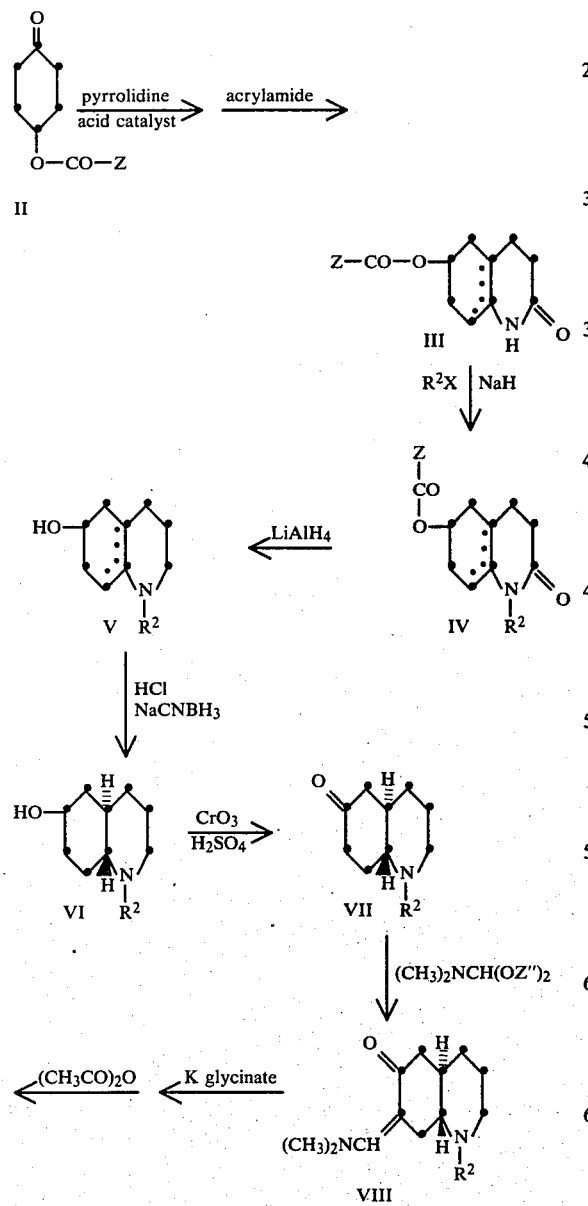

-continued
Reaction Scheme I

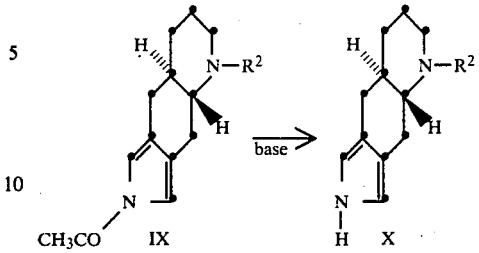

In the above reaction scheme, Z—CO is an acyl protecting group in which Z is $(C_1-C_3)$alkyl, $(C_2-C_3)$alkenyl, $(C_2-C_3)$alkynyl, $(C_5-C_6)$cycloalkyl, phenyl or substituted phenyl wherein the substituting group can be methyl, methoxy, chloro and the like, at any position of the phenyl ring. Illustratively, Z—CO can be acetyl, propionyl, butyryl, propiolyl, acrylyl, benzoyl, p-toluyl, o-chlorobenzoyl, m-methoxybenzoyl etc.

Acetals of dimethylformamide useful in producing compound VIII in Reaction Scheme I (and compound XV in Reaction Scheme II below) have the general formula $(CH_3)_2N—CH—(OZ'')_2$ in which $Z''$ is $(C_1-C_8)$alkyl, $(C_5-C_6)$cycloalkyl, $(C_3-C_4)$alkenyl, $(C_3-C_4)$alkynyl and the like. We prefer to employ one of the commercially available acetals of dimethylformamide; i.e.; the dimethyl, diethyl, diisopropyl, dibutyl, dicyclohexyl, dipropyl or dineopentyl acetals.

In accordance with Reaction Scheme I, 4-acyloxycyclohexanone (II) prepared by the procedure of E. R. H. Jones and F. Sondheimer, *J. Chem. Soc.*, 615, (1949) is reacted with pyrrolidine in the presence of an acid catalyst to yield a pyrrolidine enamine. This enamine is in turn reacted with acrylamide to produce a mixture of dl-6-acyloxy-3,4,5,6,7,8-hexahydro-2(1H)-quinolinone and dl-6-acyloxy-3,4,4a,5,6,7-hexahydro-2(1H)-quinolinone represented by formula III, the dotted lines indicating the alternative positions of the double bond.

Next, the acidic nitrogen (acidic since it is alpha to a carbonyl group) is alkylated with an alkyl halide $R^2X$ wherein $R^2$ has the same meaning as hereinabove and X is a halogen such as Cl, Br or I, in the presence of sodium hydride to yield a mixture of dl-1-$(C_1-C_3)$ alkyl (or allyl or benzyl)-6-acyloxy-3,4,5,6,7,8-hexahydro-2(1H)-quinolinone and its $\Delta^8$ isomer (IV). Reduction of this amide with lithium aluminum hydride or other suitable organometallic reducing agent yields a mixture of dl-1-$(C_1-C_3)$ alkyl (or allyl or benzyl)-6-hydroxy-1,2,3,4,5,6,7,8-octahydroquinoline and its $\Delta^8$ isomer. In this reaction mixture, conditions are encountered which serve to hydrogenolyze the acyloxy group to a hydroxyl group at C-6. The dl-1-$(C_1-C_3)$-alkyl (or allyl or benzyl)-6-hydroxyoctahydroquinoline mixture is next converted to an ammonium salt by treatment with hydrochloric acid, and the ammonium salt is then reduced with sodium cyanoborohydride to yield trans-dl-1-$(C_1-C_3)$alkyl (or allyl or benzyl)-6-hydroxydecahydroquinoline (VI). Next, the trans-dl-1-$(C_1-C_3$ alkyl, allyl, or benzyl)-6-hydroxydecahydroquinoline (VI) is oxidized using, preferably, chromium trioxide in acetic acid, to yield the corresponding 6-oxo compound (VII). By adapting the procedure of Zav'yalof et al. *C.A.*, 80, 59815z(1974), *Izv. Akad. Nauk. SSSR. Ser. Khim* 2572-7 (1973), this 6-oxo compound (VII) is reacted with dimethylformamide dimethylacetal to yield a 7-dimethylaminomethylene-6-oxo-derivative (VIII). Reaction of this derivative with potassium glycinate followed by treatment of the thus formed intermediate product with acetic anhydride yields a tricyclic derivative, trans-dl-2-acetyl-5-[($C_1$-$C_3$)alkyl, allyl or benzyl)]-4,4a,5,6,7,8-,8a,9-octahydro-2H-pyrrolo[3,4-g]quinoline (IX). Removal of the acetyl group at ·N-2 with base yields the dopamine agonist (X) when $R^2$ is ($C_1$-$C_3$)alkyl or allyl, or a useful intermediate when $R^2$ is benzyl.

Those compounds in which $R^1$ is ($C_1$-$C_3$)alkyl are prepared from compound X by taking advantage of the acidic hydrogen in the pyrrole ring and reacting an anionic salt thereof, prepared from sodium hydride or other suitable base, with an alkyl halide, $R^1 X$ where $R^1$ is ($C_1$-$C_3$) alkyl or allyl and X is Cl, Br or I.

Those compounds in which $R^2$ is benzyl can be transformed into compounds in which $R^2$ is ($C_1$-$C_3$)alkyl or allyl as follows: the benzyl group can be removed by reductive cleavage or by treatment with cyanogen bromide to yield, eventually, a compound in which $R^2$ is H. The usual conditions for removing an N-benzyl group are hydrogen with a palladium-on-carbon catalyst or reaction with cyanogen bromide followed by reductive (Zn and acetic acid) cleavage of the N-cyano compound. This debenzylated compound can then be alkylated with an allyl or a lower alkyl halide, or alternatively it may be reductively alkylated using acetaldehyde, propionaldehyde etc. with sodium cyanoborohydride.

Compounds according to Formula I above in which $R^3$ is other than H are prepared according to a slightly different, but comparable, synthetic route illustrated in Reaction Scheme II below. As in Reaction Scheme I, the synthetic procedure is illustrated for convenience with respect to a single stereoisomer (referring to the bridgehead configuration) the 4a$\beta$,8a$\alpha$ isomer.

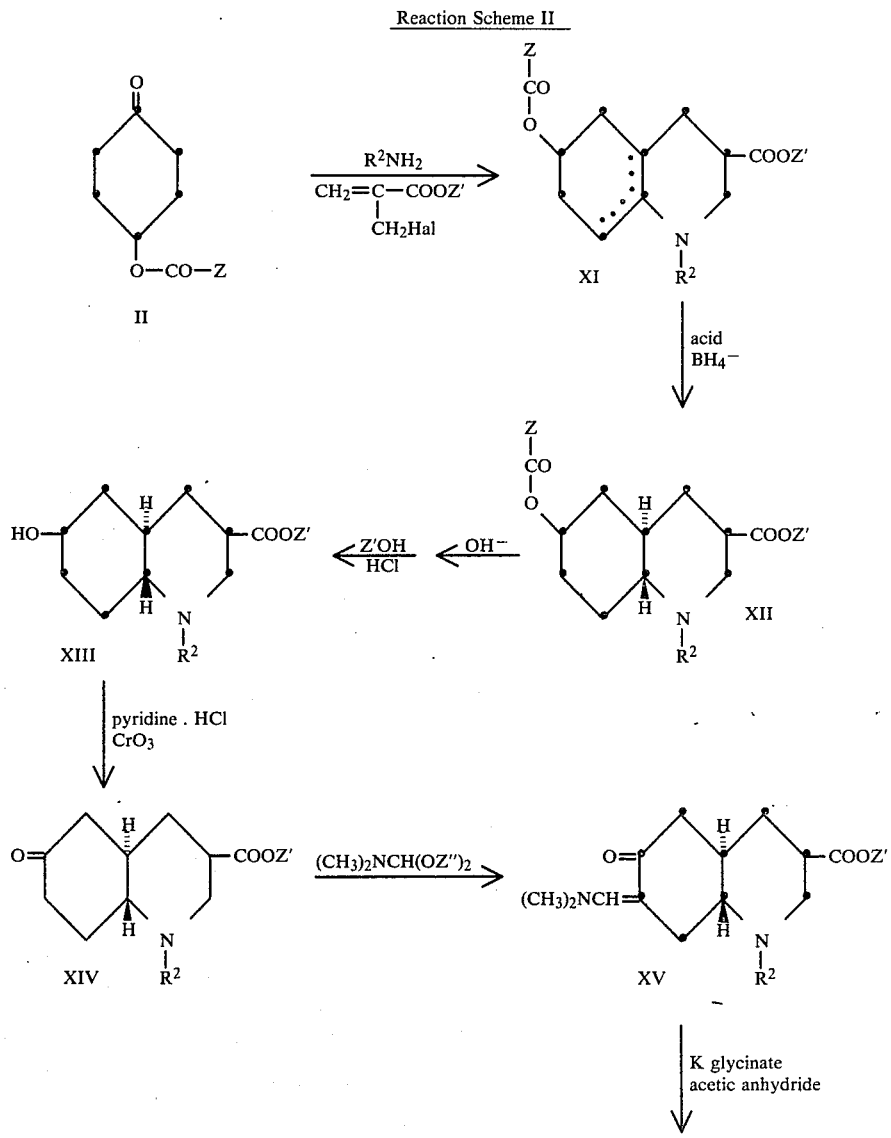

Reaction Scheme II

-continued
Reaction Scheme II

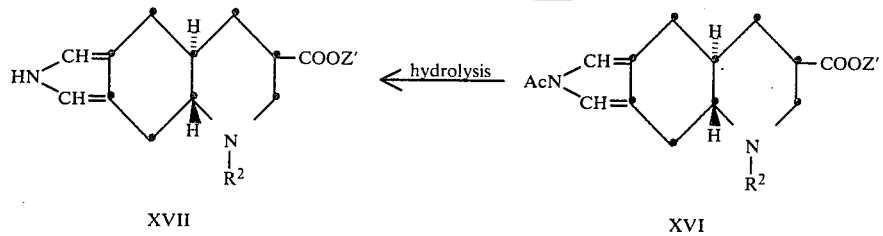

wherein Z and Z" have the same significance as in Reaction Scheme I, Hal is chloro or bromo and Z' is part of a readily hydrolyzable group Z'O—CO including $(C_1-C_2)$alkyl, phenyl substituted $(C_1-C_2)$alkyl, illustratively benzyl, phenethyl, p-methoxybenzyl, methyl, ethyl etc.

In accordance with the Reaction Scheme II, a 4-acyloxycyclohexanone (II) is reacted with an α-halomethylacrylate ester, for illustrative purposes, the ethyl ester, and an amine, $RNH_2$, wherein R is $C_1-C_3$ alkyl, allyl or benzyl. The product of this reaction is a mixture of dl-1-substituted-3-ethoxycarbonyl-6-acyloxy-1,2,3,4,5,6,7,8-octahydroquinoline and dl-1-substituted-3-ethoxycarbonyl-6-acyloxy-1,2,3,4,4a,5,6,7-octahydroquinoline represented by XI in which the dotted line indicates the alternate positions of the double bond. The hydrochloride salts of these isomers are prepared and the resulting mixture reduced with sodium cyanoborohydride to yield trans-dl-1-substituted-3-ethoxycarbonyl-6-acyloxydecahydroquinoline (XII). Hydrolysis of this diester to yield a 6-hydroxy-3-carboxylic acid followed by reesterification of the carboxylic acid group with ethanol or other alcohol in the presence of acid yields trans-dl-1-substituted-3-ethoxycarbonyl-6-hydroxydecahydroquinoline (XIII). Oxidation of the hydroxy group with Sarett's Reagent (pyridine hydrochloride and chromium trioxide) produces the corresponding 6-oxo compound (XIV). Treatment of this 6-oxo derivative with dimethylformamide dimethylacetal results in reaction at C-7 (adjacent to the keto group) to give trans-dl-1-substituted-3-ethoxycarbonyl-6-oxo-7-(dimethylaminomethylene)decahydroquinoline (XV). Reaction of this derivative with potassium glycinate followed by a treatment of the intermediate product with acetic anhydride gives the tricyclic derivative, trans-dl-2-acetyl-5-substituted-7-ethoxycarbonyl-4,4a,5,6,7,8,8a,9-octahydro-2H-pyrrolo[3,4-g]quinoline (XVI). Hydrolysis with sodium ethoxide in ethanol yields the NH compound (XVII).

The octahydropyrrolo[3,4-g]quinoline of Formula XVI represents a single isomer. The mirror image of XVI is produced concomitantly and is included within the scope of this invention. We believe, based upon analogy with the D-ergolines, that the diastereoisomer XVI as drawn is the isomer having dopamine agonist activity. The trans-dl racemate, which contains XVI and its mirror image, is of course useful as a dopamine agonist, even though most of the desired activity resides in one of its component stereoisomers.

Compounds according to XVI above in which $R^2$ is methyl or benzyl can be transformed into compounds in which $R^2$ is ethyl, allyl or n-propyl by reaction with cyanogen bromide. The intermediate 5-cyano derivative can be reductively cleaved (zinc plus acetic acid) to yield a compound in which $R^2$ is H. In addition, the benzyl group can be removed by hydrogenation with palladium-on-carbon to yield those intermediates in which $R^2$=H. Alkylation of those compounds in which $R^2$ is H can be accomplished by reaction with an alkyl halide, $R^2Cl$, $R^2Br$ or $R^2I$. Alternatively, the secondary amine can be reacted with acetaldehyde, acrolein, or propionaldehyde under reducing conditions ($NaBH_3CN$) to yield an N-ethyl, N-allyl or N-n-propyl derivative.

Intermediates described in Reaction Schemes I and II, having the following structures

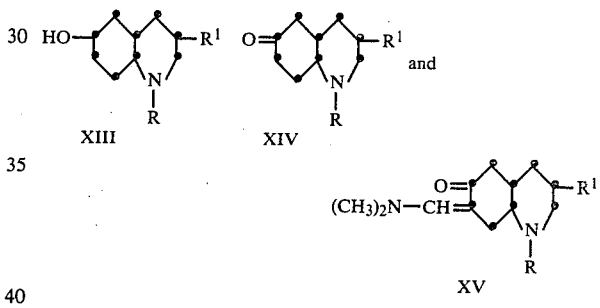

wherein R is $(C_1-C_3)$ alkyl, allyl or benzyl and $R^1$ is COOZ' (wherein Z' is $(C_1-C_2)$alkyl or phenylsubstituted $(C_1-C_2)$alkyl) in XIII and XIV and H or COOZ' in XV are claimed in our copending application, Ser. No. 031,641 filed this even date, now U.S. Pat. No. 4,198,415, issued Apr. 15, 1980. These intermediates are prepared by the methods set forth in the above Reaction Schemes, in the accompanying detailed description and in the Examples which follow.

The dopamine agonists of this invention in which $R^3$ is other than H; i.e. those compounds in which $R^3$ is $CH_2X$ wherein X is CN, $OCH_3$, $SCH_3$, $SO_2CH_3$ or $CO—NH_2$, are prepared according to Reaction Scheme III below Reaction Scheme III

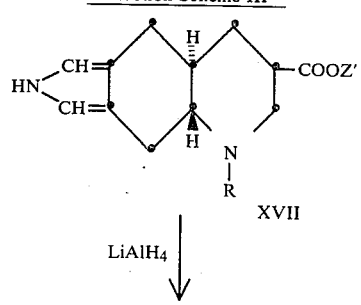

$LiAlH_4$

-continued
Reaction Scheme III

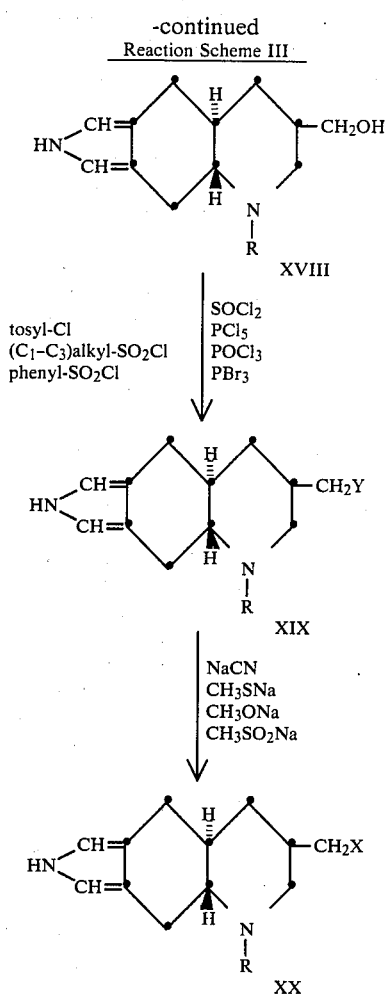

wherein Z' and R have the same significance as before, Y is a "leaving" group: Cl, Br, OSO$_2$phenyl, O-tosyl or SO$_2$(C$_1$–C$_3$)alkyl, R$^2$ is H, SO$_2$phenyl, tosyl or SO$_2$(-C$_1$–C$_3$)alkyl, and X is CN, SCH$_3$, OCH$_3$ or SO$_2$CH$_3$. The acetyl group of a compound according to XVI in Reaction Scheme II is hydrolyzed with sodium ethoxide in ethanol or sodium methoxide in methanol to yield a desacetyl derivative. The carboalkoxy group is then reduced with a metal hydride such as LiAlH$_4$ to an hydroxymethyl group, thus providing a trans-dl-5-substituted-7-hydroxymethyl-4,4a,5,6,7,8,8a,9-octahydro-2H-pyrrolo[3,4-g]quinoline (XVIII). The hydroxyl can be replaced with a chlorine or bromine leaving group and the resulting chloromethyl or bromomethyl compound reacted with NaCN to yield a compound in which R$^3$ is CH$_2$—CN. Other leaving groups—groups readily replaced by a nucleophilic reagent—such as the mesyloxy, p-tosyloxy, benzenesulfonyloxy and the like groups [when X in Formula I, Ia or Ib or Y in Formula XIX, is OSO$_2$(C$_1$–C$_3$)alkyl, OSO$_2$phenyl or OSO$_2$tolyl] can be produced by acylation of the hydroxy group with a sulfonyl halide. Reaction of the thusproduced compound with sodium methylate, methylmercaptan sodium salt, sodium cyanide, sodium methanesulfinate or other basic salts of methanol, methyl mercaptan etc. yields compounds according to Formula I, Ia or Ib in which R$^3$ is CH$_2$X and X is SCH$_3$, OCH$_3$, CN or SO$_2$CH$_3$. Compounds in which X is CONH$_2$ are prepared by hydration of the corresponding cyano compound.

Compounds represented by Formulas I, Ia and Ib, in which R$^2$ is H and by Formula IX, and X above have two centers of assymetry, the ring junction carbons at 8a and 4a. Thus, the compounds can occur as two racemates, ordinarily denominated as the trans-dl racemate and the cis-dl racemate. It is believed, however, according to the best evidence from $^{13}$C NMR spectral data of the maleate salt of the compound according to Formula X above wherein R$^2$ is benzyl, that the cyanoborohydride reduction (going from V to VI in Reaction Scheme I) yields a transfused decahydroquinoline. While the arguments for the trans configuration based upon $^{13}$C NMR spectral data are compelling, an X-ray crystallographic investigation has also been carried out on the nicely crystalline enaminoketone (VIII) in which R$^2$ is methyl, the precursor of the pyrrole (X). This x-ray analysis indicated clearly that the ring junction is trans. Thus, only the trans racemate is prepared by the synthetic procedures disclosed herein and the compounds of this invention are preferably represented as the trans-dl steroisomers Ia and Ib above in which R$^3$ is H. Resolution of this racemate into its optical antipodes can be accomplished by procedures known to those skilled in the art, and the individual trans-d and trans-l isomers are included within the scope of this invention.

When R$^3$ is other than H, a third chiral center is introduced at C-7, thereby doubling, at least in theory, the number of isomers produced by Reaction Schemes II and III. However, it is presently believed that the configuration of the C-7 group is "trans" to that of the 8a hydrogen. Thus in Ia above, R$^3$ when it is other than H, has a beta configuration with the 8a hydrogen having an alpha configuration. In the mirror image Ib, the 8a hydrogen is beta and the C-7 substituent alpha. Thus the dl-trans-7-substituted octahydropyrrolo[3,4-g]quinolines of this invention are provided substantially as a single racemate.

In addition, it is apparent from an inspection of the dl-trans-1(substituted)-6-keto decahydroquinoline (VII) that reaction with dimethylformamide dimethylacetal could take place at either C-5 or C-7 since both these carbons are ortho to the ketone group and are thus "activated". The same x-ray crystallographic analysis of the enamine (VIII) clearly indicated that reaction had taken place at C-7 rather than C-5. Hence, the final tricyclic compounds IX, X, XVI and I are the linear pyrrolo[3,4-g]quinolines rather than the angular tricyclic compounds (which would be named as 4,4a,5,6,7,8-,8a,9-octahydro-1H-pyrrolo[2,3-i]quinolines).

This invention is further illustrated by the following specific examples.

EXAMPLE 1

Preparation of trans-dl-2-Acetyl-5-methyl-4,4a,5,6,7,8,8a,9-octahydro-2H-pyrrolo[3,4-g]quinoline A reaction mixture was prepared from 52 g. of 4-benzoyloxycyclohexanone, 30 ml. of pyrrolidine, a few crystals of p-toluene sulfonic acid monohydrate, and 1000 ml. of benzene. The reaction mixture was heated to refluxing temperature under a nitrogen atmosphere for one hour in an apparatus equipped with a Dean-Stark water trap. The reaction mixture was then cooled and the solvent and other volatile materials removed by evaporation in vacuo. The residue, comprising the pyrrolidine enamine of 4-benzoyloxycyclohexanone formed in the above reaction was dissolved without further purification in 1000 ml. of dioxane. 42.6 g. of acrylamide were added. This new reaction mixture was heated under a nitrogen atmosphere at reflux temperature for twenty-one hours. Thin-layer chromatography of the reaction mixture indicated one major spot. The reaction mixture was cooled and the volatile constituents removed by evaporation in vacuo. A chloroform solution of the residue comprising 6-benzoyloxy-3,4,5,6,7,8-hexahydro-1H-quinolin-2-one and the isomeric product 6-benzoyloxy-3,4,4a,5,6,7-hexahydro-1H-quinolin-2-one was chromatographed over 350 g. of florisil using chloroform containing increasing quantities of ethanol (0 to 2 percent) as the eluant. Fractions found to contain 6-benzoyloxy-3,4,5,6,7,8-hexahydro-1H-quinolin-2-one and its isomer by thin-layer chromatography were combined and the solvent removed therefrom in vacuo. The resulting residue was crystalized by triturating with hexane to yield a crystalline mixture of 6-benzoyloxy-3,4,5,6,7,8-hexahydro-1H-quinolin-2-one and the corresponding 3,4,4a,5,6,7-hexahydro derivative. The mixture melted in the range 130°–150° C. after recrystallization from an ether-hexane solvent mixture.

Analysis: Calculated: C, 70.83; H, 6.32; N, 5.16; Found: C, 71.05; H, 6.19; N, 5.33.

NMR of the product isolated above indicated that the mixture contained about 60 percent of 6-benzoyloxy-3,4,5,6,7,8-hexahydro-1H-quinolin-2-one and 40% of the 3,4,4a,5,6,7-hexahydro isomer.

46.5 g. of the above isomer mixture were dissolved in 400 ml. of tetrahydrofuran (THF). 80 ml. of methyl iodide were added and the resulting mixture cooled in an ice-water bath. 9.6 g. of sodium hydride (as a 50 percent suspension in mineral oil) were added in portions. After all of the sodium hydride suspension had been added, the cooling bath was removed and the reaction mixture stirred at ambient temperature under a nitrogen atmosphere for about 4 hours. The reaction mixture was then diluted with water and the aqueous mixture thoroughly extracted with chloroform. The chloroform extracts were combined and the combined extracts washed with saturated aqueous sodium chloride and dried. The chloroform was removed by evaporation to dryness in vacuo leaving as a residue an orange oil weighing 47.3 g. Recrystallization from an ether-hexane solvent mixture yielded crystals of 1-methyl-6-benzoyloxy-3,4,5,6,7,8-hexahydro-2(1H)-quinolinone and the corresponding 3,4,4a,5,6,7-hexahydro isomer.

Analysis: Calculated: C, 71.56; H, 6.71; N, 4.91; Found: C, 71.33; H, 6.90; N, 4.67.

Following the above procedure, 59 g. of a mixture of 6-benzoyloxy-3,4,5,6,7,8-hexahydro-2(1H)-quinolinone and 6-benzoyloxy-3,4,4a,5,6,7-hexahydro-2(1H)-quinolinone were reacted with n-propyl iodide in the presence of sodium hydride to yield 1-n-propyl-6-benzoyloxy-3,4,5,6,7,8-hexahydro-2(1H)-quinolinone and the corresponding 3,4,4a,5,6,7-hexahydro isomer. The compounds were purified by chromatography over florisil using an ether-chloroform solvent mixture as the eluant. Also following the above procedure, a mixture of the 1-benzyl-6-benzoyloxyhexahydro-2(1H)-quinolinones was prepared by substituting benzyl bromide for methyl iodide.

A solution of 47.3 g. of 1-methyl-6-benzoyloxy-3,4,5,6,7,8-hexahydro-2(1H)-quinolinone and the corresponding 3,4,4a,5,6,7-hexahydro isomer as obtained above were dissolved in 800 ml. of THF and the solution cooled to about 0° C. 20 g. of lithium aluminum hydride were added thereto in portions and the resulting mixture refluxed for four hours under a nitrogen atmosphere. The reaction mixture was cooled and excess lithium aluminum hydride destroyed by the addition of ethyl acetate. 10% sodium hydroxide was then added and the mixture diluted with water to decompose any organometallics present. The aqueous mixture was extracted several times with a chloroform-isopropanol solvent mixture. The organic extracts were combined and the combined extracts washed with saturated aqueous sodium chloride and then dried. Evaporation of the solvent yielded as a residue a mixture of the enamines—1-methyl-6-hydroxy-1,2,3,4,5,6,7,8-octahydroquinoline and 1-methyl-6-hydroxy-1,2,3,4,4a,5,6,7-octahydroquinoline-formed in the above reaction. (The lithium aluminum hydride reduction served to remove the benzoyl group at C-6 as a benzyl alcohol moiety, leaving a free hydroxyl in that position of the ring). The above residue, without further purification, was dissolved in about 300 ml. of ether and the ethereal solution saturated with gaseous hydrogen chloride, thus forming the hydrochloride salt of the enamine mixture. The ether was removed by decantation and the residue dissolved in a mixture of 200 ml. of THF and 50 ml. of methanol. This solution was cooled in an ice water bath. 12 g. of sodium cyanoborohydride were added with cooling and stirring. After all of the cyanoborohydride had been added, the reaction mixture was stirred for another 60 minutes and then poured over a mixture of ice and 1 N aqueous hydrochloric acid. The acidic aqueous solution was extracted with chloroform and the chloroform extract discarded. The solution was then made basic with 14 N aqueous ammonium hydroxide. Trans-dl-1-methyl-6-hydroxydecahydroquinoline formed in the above reaction, being insoluble in the alkaline medium, separated and was extracted several times with a chloroformisopropanol solvent mixture. The combined extracts were washed with saturated aqueous sodium chloride and then dried. Evaporation of the solvent yielded 15 g. of trans-dl-1-methyl-6-hydroxydecahydroquinoline.

Following the above sequence of reactions, a mixture of 1-n-propyl-6-benzoyloxy-3,4,5,6,7,8-hexahydro-2(1H)-quinolinone and the corresponding 3,4,4a,5,6,7-hexahydro isomer were first reduced with lithium aluminum hydride to yield a mixture of $\Delta^{4a}$ and $\Delta^8$ 1-n-propyl-6-hydroxyoctahydroquinolines which was converted by treatment with ethereal hydrogen chloride to the enamine hydrochloride. Reduction of this intermediate enamine hydrochloride with sodium cyanoborohydride yielded trans-dl-1-n-propyl-6-hydroxydecahydroquinoline (56 g. of starting material yielded 30 g. of product). Also following the above procedure, 1-benzyl-6-benzoyloxy-3,4,5,6,7,8-hexahydro-2-(1H)-quinolinone in admixture with 1-benzyl-6-benzoyloxy-3,4,4a,5,6,7-hexahydro-2(1H)-quinolinone was reduced with lithium aluminum hydride to yield the corresponding 1-benzyl-6-hydroxy-1,2,3,4,5,6,7,8-octahydroquinoline and 1-benzyl-6-hydroxy-1,2,3,4,4a,5,6,7-octahydroquinoline as a mixture, treatment of which with ethereal hydrogen hydrochloride yielded the enamine salt. Reduction of the enamine salt with sodium cyanoborohydride gave 1-benzyl-6-hydroxydecahydroquinoline (65 g. of starting mixture yielded 49.6 g. of final product).

Fifteen grams of trans-dl-1-methyl-6-hydroxydecahydroquinoline were dissolved in 250 ml. of 6 N aqueous sulfuric acid. The solution was cooled in an ice-water bath. A solution of 9 g. of chromium trioxide in 60 ml. of 6 N aqueous sulfuric acid were added thereto with stirring in dropwise fashion over a 10-minute period. The cooling bath was removed and the reaction mixture stirred for an additional 60 minutes at ambient temperature. The excess oxidizing agent was decomposed by adding isopropanol to the reaction mixture. The reaction mixture was next poured over ice and the acidic aqueous solution made basic with 14 N aqueous ammonium hydroxide. trans-dl-1-Methyl-6-oxodecahydroquinoline thus formed, being insoluble in the alkaline layer, separated and was extracted several times with a mixture of chloroform and isopropanol. The extracts were combined and the combined extracts washed with saturated aqueous sodium chloride and then dried. Evaporation of the solvent in vacuo yielded trans-dl-1-methyl-6-oxodecahydroquinoline boiling in the range 105°–116° C. at 6 torr; yield=7.7 g. (45%).

Following the above procedure, 29.5 g. of trans-dl-1-n-propyl-6-hydroxydecahydroquinoline were dissolved in 300 ml. of glacial acetic acid to which was added 8 ml. of 18 N aqueous sulfuric acid. 55 ml. of a solution of 26.7 g. of chromium trioxide in 23 ml. of 18 M sulfuric acid were added in dropwise fashion. trans-dl-1-n-Propyl-6-oxodecahydroquinoline formed in the above reaction was isolated by the above procedure; yield=21.4 g. Still following the above procedure, 49.6 g. of trans-dl-1-benzyl-6-hydroxy-decahydroquinoline were oxidized with chromium trioxide in sulfuric acid to yield trans-dl-1-benzyl-6-oxodecahydroquinoline; yield=21.1 g. of a dark oil.

A reaction mixture was prepared from 7.7 g. of trans-dl-1-methyl-6-oxodecahydroquinoline, 36 g. of the dimethyl acetal of dimethylformamide and 250 ml. of benzene. Benzene was removed by distillation at atmospheric pressure under nitrogen until about ½ the original volume remained (1.25 hours). Sufficient benzene was then added to make up the volume to the original volume and the process was repeated (four times). All of the benzene was finally removed by evaporation in vacuo and the resulting residue dissolved in 100 g. of dimethylformamide dimethylacetal. This solution was heated to refluxing temperature under nitrogen for 20 hours. The reaction mixture was then evaporated in vacuo and a chloroform solution of the residue chromatographed over 150 g. of florisil using as the eluant, methylene dichloride containing increasing amounts (1–5%) of methanol. Fractions containing similar compounds as shown by TLC were combined. The third substance to come off the column was a yellow solid (wt=3 g.) The solid was heated with 100 ml. of ether and the resulting solution filtered. Concentration of the filtrate to about 50 ml. yielded 590 mg. of trans-dl-1-methyl-6-oxo-7-dimethylaminomethylenedecahydroquinoline melting at 107°–109° C.

Analysis: Calculated: C, 70.23; H, 9.97; N, 12.60; Found: C, 70.17; H, 9.74; N, 12.87.

The above reaction was repeated except that trans-dl-1-n-propyl-6-oxodecahydroquinoline was used as a starting material and the product was chromatographed over florisil using chloroform containing increasing quantities of methanol (1–5%) as the eluant. trans-dl-1-n-Propyl-6-oxo-7-dimethylaminomethylenedecahydroquinoline was obtained.

Following the above procedure, trans-dl-1-benzyl-6-oxodecahydroquinoline was reacted with dimethylformamide dimethylacetal to yield trans-dl-1-benzyl-6-oxo-7-dimethylaminomethylenedecahydroquinoline melting at 109°–111° C. after recrystallization from an ether-hexane solvent mixture.

Analysis: Calculated: C, 76.47; H, 8.78; N, 9.29; Found: C, 76.25; H, 8.66; N, 9.36.

The potassium salt of glycine was prepared by reacting 975 mg. of glycine with 730 mg. of potassium hydroxide in 100 ml. of anhydrous ethanol. 2.8 g. of trans-dl-1-methyl-6-oxo-7-dimethylaminomethylenedecahydroquinoline were added and the resulting mixture heated at reflux temperature under nitrogen for about 3 hours. The reaction mixture was cooled, the volatile constituents removed in vacuo and the residue diluted with ether. The resulting mixture was filtered and the adduct weighed 3.5 g. The glycine adduct was then cyclized, decarboxylated and acetylated by heating with 100 ml. of acetic anhydride at reflux temperature under nitrogen for about 45 minutes. The acetylation mixture was cooled and the volatile constituents removed by evaporation to dryness. The residue, comprising trans-dl-2-acetyl-5-methyl-4,4a,5,6,7,8,8a,9-octahydro-2H-pyrrolo[3,4-g]quinoline was suspended in methylene dichloride and the suspension filtered to yield 1.7 g. of solid. The methylene dichloride filtrate was chromatographed over 150 g. of florisil using methylene dichloride containing increasing (0–5%) amounts of methanol as the eluant. Fractions shown by TLC to contain the same substance were combined, and the combined fractions washed with sodium bicarbonate and saturated aqueous sodium chloride and then dried. Evaporation of the solvent in vacuo yielded a residue which was rechromatographed over 30 g. of florisil using chloroform containing 5% methanol as the eluant. Fractions shown by TLC to contain the same substance were combined to yield 1.72 g. of a viscous orange oil comprising purified trans-dl-2-acetyl-5-methyl-4,4a,5,6,7,8,8a,9-octahydro-2H-pyrrolo[3,4-g]quinoline. The orange oil was dissolved in ether and a solution of 870 mg. of maleic acid in ether added thereto. The maleate salt thus formed melted at 201°–203° C. after recrystallization from methanol ether solvent mixture (1:2).

Analysis: Calculated: C, 62.05; H, 6.94; N, 8.04; Found: C, 61.81; H, 6.82; N, 7.97.

Following the above procedure, trans-dl-2-acetyl-5-n-propyl-4,4a,5,6,7,8,8a,9-octahydro-2H-pyrrolo[3,4-g]quinoline was prepared from trans-dl-2-n-propyl-6-oxo-7-dimethylaminomethylenedecahydroquinoline by reaction with the potassium salt of glycine followed by acetic anhydride. The compound was purified by chromatography.

Following the above procedure, trans-dl-1-benzyl-6-oxo-7-dimethylaminomethylenedecahydroquinoline was reacted with the potassium salt of glycine and acetic anhydride to yield trans-dl-2-acetyl-5-benzyl-4,4a,5,6,7,8,8a,9-octahydro-2H-pyrrolo[3,4-g]quinoline. This latter derivative was purified by chromatography over florisil and then converted to the maleate salt. Trans-dl-2-acetyl-5-benzyl-4,4a,5,6,7,8,8a,9-octahydro-2H-pyrrolo[3,4-g]quinoline maleate melted at 162°–164° C. after recrystallization from a methanol-ether solvent mixture.

Analysis: calc.: C, 67.91; H, 6.65; N, 6.60; Found: C, 67.76; H, 6.40; N, 6.58.

EXAMPLE 2

Preparation of trans-dl-5-Methyl-4,4a,5,6,7,8,8a,9-octahydro-2H-pyrrolo[3,4-g]quinoline from the Corresponding 2-Acetyl Compound.

One and two-tenths grams of trans-dl-2-acetyl-5-methyl-4,4a,5,6,7,8,8a,9-octahydro-2H-pyrrolo[3,4-g]quinoline maleate were suspended in 100 ml. of methanol and 10 ml. of 2 N aqueous sodium hydroxide were added. The resulting mixture was stirred at room temperature under a nitrogen atmosphere for about 35 minutes and was then diluted with dilute aqueous sodium hydroxide. The resulting alkaline solution was extracted several times with chloroform. The chloroform extracts were combined and the combined extracts washed with saturated aqueous sodium chloride and dried. Evaporation of the chloroform yielded 400 ml. of crystalline material melting at 190°–6° C. with decomposition. A chloroform solution of the material was then chromatographed over 30 g. of florisil using chloroform containing increasing amounts (2–5%) of methanol as the eluant. The second major component to be eluted from the column consisting of trans-dl-5-methyl-4,4a,5,6,7,8,8a,9-octahydro-2H-pyrrolo[3,4-g]quinoline. Fractions containing this compound were combined and the solvent removed from the combined fractions by evaporation. Recrystallization of the residue from ether yielded trans-dl-5-methyl-4,4a,5,6,7,8,8a,9-octahydro-2H-pyrrolo[3,4-g]quinoline melting at 200°–222° C. with decomposition (80 mg.).

Analysis: calc.: C, 75.74 H, 9.53; N, 14.72; Found: C, 75,88 H, 9.28; N, 14.55.

Following the above procedure, trans-dl-2-acetyl-5-n-propyl-4,4a,5,6,7,8,8a,9-octahydro-2H-pyrrolo[3,4-g]quinoline (4.8 g) was hydrolyzed with dilute aqueous sodium hydroxide. trans-dl-5-n-Propyl-4,4a,5,6,7,8,8a,9-octahydro-2H-pyrrolo[3,4-g]quinoline thus prepared was purified by chromotography over florisil using chloroform containing increasing amounts (2–10%) methanol as the eluant. Fractions shown to contain the desired product by TLC were combined and the solvent evaporated therefrom. Recrystallization of the residue from a methanol-ether solvent mixture yielded 245 mg. crystalline trans-dl-5-n-propyl-4,4a,5,6,7,8,8a,9-octahydro-2H-pyrrolo[3,4-g]quinoline melting at 169°–171° C. with decomposition; nmr peaks at 52, 384 and 510 cps. (in CDCl$_3$).

Analysis: calc.: C, 64.65; H, 7.84; N, 8.38; Found: C, 64.40; H, 7.62; N, 8.12.

EXAMPLE 3

Alternate Preparation of trans-dl-5-n-Propyl-4,4a,5,6,7,8,8a,9-octahydro-2H-pyrrolo[3,4-g]quinoline A solution was prepared from 2.5 g. of trans-dl-2-acetyl-5-benzyl-4,4a,5,6,7,8,8a,9-octahydro-2H-pyrrolo[3,4-g]quinoline and 200 ml. of methylene dichloride. 4 g. of cyanogenbromide were added and the resulting mixture was stirred at ambient temperature under a nitrogen atmosphere for about 16 hours. Volatile constituents were removed by evaporation in vacuo. A chloroform solution of the residue containing trans-dl-1-acetyl-5-cyano-4,4a,5,6,7,8,8a,9-octahydro-2H-pyrrolo[3,4-g]quinoline formed in the above reaction was chromatographed over 200 g. of florisil using chloroform as the eluant. Fractions shown to contain the desired compound were combined and the solvent removed therefrom. Recrystallization of the residue from ether yielded crystalline trans-dl-2-acetyl-5-cyano-4,4a,5,6,7,8,8a,9-octahydro-2H-pyrrolo[3,4-g]quinoline melting at 135°–7° C. (total yield = 630 mg.)

A mixture of 0.6 g. of trans-dl-2-acetyl-5-cyano-4,4a,5,6,7,8,8a,9-octahydro-2H-pyrrolo[3,4-g]quinoline, 50 ml. of glacial acetic acid, 10 ml. of water and 3 g. zinc dust was heated at refluxing temperature under a nitrogen atmosphere for about 7 hours. The reaction mixture was then filtered and the filtrate poured over ice. The aqueous filtrate was then made basic with 14 N aqueous ammonium hydroxide. The aqueous alkaline layer was extracted several times with a mixture of chloroform and isopropanol. The organic extracts were combined and the combined extracts washed with saturated aqueous sodium chloride and then dried. Evaporation of the solvent in vacuo yielded a residue which was shown to be one-spot material by TLC. The residue was dissolved in 50 ml. of dimethylformamide to which was added 0.8 g. potassium carbonate and 0.4 ml. of n-propyl iodide. This reaction mixture was stirred at ambient temperature under a nitrogen atmosphere for about 16 hours. The reaction mixture was then diluted with water and the diluted mixture extracted with ethyl acetate. The ethyl acetate extract was washed with water and saturated aqueous sodium chloride and then dried. Evaporation of the solvent in vacuo yielded a residue shown to contain one major spot by TLC. This residue was dissolved in 20 ml. of methanol to which was added 3 ml. of 2 N aqueous sodium hydroxide. This reaction mixture was stirred at ambient temperature under a nitrogen atmosphere for 65 min. The reaction mixture was diluted with water and the diluted mixture extracted several times with chloroform. The chloroform extracts were combined and the combined extracts washed with saturated aqueous sodium chloride and then dried. Evaporation of the chloroform yielded a residue which was shown to contain one major spot by TLC. An ether solution of the residue, comprising trans-dl-5-n-propyl-4,4a,5,6,7,8,8a,9-octahydro-2H-pyrrolo[3,4-g]quinoline formed in the above reaction, was treated with an excess of maleic acid in ether solution, thus forming the maleate salt of the base. The maleate salt was separated by filtration and recrystallized from an ether-methanol solvent mixture. trans-dl-5-n-Propyl-4,4a,5,6,7,8,8a,9-octahydro-2H-pyrrolo[3,4-g]quinoline maleate thus prepared melted 168°–170° C., with decomposition; yield = 215 mg.

EXAMPLE 4

Preparation of trans-dl-4,4a,5,6,7,8,8a,9-Octahydro-2H-pyrrolo[3,4-g]quinoline 3.5 Grams of trans-dl-2-acetyl-5-benzyl-4,4a,5,6,7,8,,8a,9-octahydro-2H-pyrrolo[3,4-g]quinoline were dissolved in 196 ml. of ethanol to which solution was added 0.5 g. of a 5% palladium-on-carbon catalyst. The mixture was hydrogenated in an Adams machine at room temperature at an initial hydrogen pressure of 60 psi. After 2 hours, 100% of the theoretical amount of hydrogen had been absorbed. The hydrogenation mixture was removed from the machine and the catalyst separated by filtration. TLC indicated that there were two major spots, one being starting material. The filtrate was concentrated in vacuo to yield crystalline material. Concentration of the filtrate yielded a further batch of crystalline material. These two batches were combined, dissolved in water and the aqueous solution made basic with 14 N aqueous ammonium hydroxide. The alkaline layer was extracted several times with a mixture of chloroform and isopropanol. The organic extracts were combined and the combined extracts were washed with saturated aqueous sodium chloride and dried. Evaporation of the solvent yielded a residue comprising trans-dl-2-acetyl-4,4a,5,6,7,8,8a,9-octahydro-2H-pyrrolo[3,4-g]quinoline formed in the above hydrogenation. The residue was washed with hexane. It melted at 89°–91° C. The maleate salt was prepared by dissolving the residue in ether and adding an excess of maleic acid in ether. The maleate salt was recrystallized from a mixture of methanol and ether and melted at 150°–1° C.

Three-tenths grams of trans-dl-2-acetyl-4,4a,5,6,7,8,8a,9-octahydro-2H-pyrrolo[3,4-g]quinoline were dissolved in 15 ml. methanol to which was added 2 ml. of 2 N aqueous sodium hydroxide. The hydrolysis mixture was stirred at ambient temperature under nitrogen for ¾ hour. The reaction mixture was then diluted with water and the alkaline layer extracted with a mixture of chloroform and isopropanol. The organic extract was separated, washed with saturated aqueous sodium chloride and then dried. Evaporation of the solvent yielded a residue showing a single spot by TLC. The residue was dissolved in ether and an excess of an ethereal solution of maleic acid added thereto. The resulting gummy precipitate was separated, dissolved in methanol, and the methanol solution diluted with ether to yield crystalline material. trans-dl-4,4a,5,6,7,8,8a,9-Octahydro-2H-pyrrolo[3,4-g]quinoline maleate thus prepared melted at 190° C. with decomposition.

EXAMPLE 5

Alternate Preparation of
1-n-Propyl-6-benzoyloxy-3,4,5,6,7,8-hexahydro-2(1H)-quinolinone and
1-n-Propyl-6-benzoyloxy-3,4,4a,5,6,7-hexahydro-2(1H)-quinolinone A reaction mixture was prepared containing 4.4 g. of 4-benzoyloxycyclohexanone [prepared by the procedure of E. R. H. Jones and F. Sondheimer, *J. Chem. Soc.*, 615 (1949)], 2.5 ml. of n-propylamine and 100 ml. of toluene. The mixture was heated to reflux temperature in a nitrogen atmosphere using a Dean Stark water trap for about 2 hours. The reaction mixture was then heated to refluxing temperature for an additional 2 hours in the presence of a molecular sieve to remove water. The reaction mixture was then cooled and the solvent removed by evaporation in vacuo. 4 ml. of methyl acrylate and 100 ml. of dioxane were added to the residue which was then refluxed overnight under a nitrogen atmosphere. The reaction mixture was again cooled and the volatile constituents removed by evaporation in vacuo. Chromatography of an ethereal solution of the resulting residue over 200 g. of florisil using ether as an eluant yielded a mixture of 1-n-propyl-6-benzoyloxy-3,4,5,6,7,8-hexahydro-2(1H)-quinolinone and 1-n-propyl-6-benzoyloxy-3,4,4a,5,6,7-hexahydro-2(1H)-quinolinone: yield=2.15 g.

EXAMPLE 6

Preparation of
trans-dl-2-Acetyl-5-n-propyl-7-ethoxycarbonyl-4,4a,5,6,7,8,8a,9-octahydropyrrolo[3,4-g]quinoline A mixture of 10 ml. of n-propyl amine and 400 ml. of toluene were cooled in an ice-water bath. A solution of 16.5 g. of ethyl α-(bromomethyl)acrylate in 50 ml. of toluene was added thereto in dropwise fashion. The resulting mixture was stirred with cooling for about 25 minutes. Next, a solution of 11 g. of 4-benzoyloxycyclohexanone in 75 ml. of toluene was added in dropwise fashion. This new mixture was heated under a nitrogen atmosphere to refluxing temperature for about 23 hours. The reflux condenser was equipped with a Soxhlet extractor containing a 5 A sieve to remove water. Next the reaction mixture was cooled and the cooled mixture filtered. Evaporation of the filtrate yielded a residue comprising a mixture of 1-n-propyl-3-ethoxycarbonyl-6-benzoyloxy-1,2,3,4,5,6,7,8-octahydroquinoline and 1-n-propyl-3-ethoxycarbonyl-6-benzoyloxy-1,2,3,4,4a,5,6,7-octahydroquinoline. The residue was dissolved in an etherchloroform solvent mixture and the resulting solution saturated with gaseous hydrogen chloride while maintaining the temperature in the range 0°–5° C. The solvent was decanted from the crystalline hydrochloride salts thus formed. The salts were dissolved in 100 ml. of methanol. 300 ml. of THF were added and the resulting solution cooled in an ice-water bath. 15 g. of sodium cyanoborohydride were added in portions to the stirred and cooled reaction mixture. After the addition had been completed, the reaction mixture was stirred for another 1.25 hours after which time it was diluted with aqueous sodium bicarbonate. The aqueous alkaline mixture was extracted several times with ethyl acetate. The ethyl acetate extracts were combined and the combined extracts washed with saturated aqueous sodium chloride solution and then dried. Evaporation of the solvent yielded trans-dl-1-n-propyl-3-ethoxycarbonyl-6-benzoyloxydecahydroquinoline. The compound was dissolved in a mixture of 400 ml. of methanol and 100 ml. of 2 N aqueous sodium hydroxide. This mixture was stirred at ambient temperature under a nitrogen atmosphere for 64 hours after which time the volatile constituents were removed by evaporation in vacuo. The resulting residue was suspended in 800 ml. of ethanol and 15 ml. of 12 N aqueous hydrochloric acid. The esterification mixture was heated to refluxing temperature and about 300 ml. of solvent removed by distillation. 300 ml. of additional ethanol were added and the reaction mixture heated to refluxing temperature for 26 hours in an apparatus equipped with a Soxhlet trap containing a 3 A sieve. The reaction mixture was cooled, diluted with aqueous sodium bicarbonate and the alkaline mixture extracted several times with chloroform. The chloroform extracts were combined and the combined extracts washed with saturated aqueous sodium chloride and then dried. Evaporation of the chloroform yielded 10.3 g. of a residue which was purified by chromatography over 150 g. of florisil using chloroform containing increasing (2–10%) of methanol as the eluant. Trans-dl-1-n-propyl-3-ethoxycarbonyl-6-hydroxydecahydroquinoline formed in the above reaction was obtained from the eluate fractions as a purified product.

A solution was prepared from 8.8 g. of trans-dl-1-n-propyl-3-ethoxycarbonyl-6-hydroxydecahydroquinoline and 400 ml. of methylene dichloride. 41 g. of sodium acetate were added. Next, 10.8 g. of pyridine hydrochloride:chromium trioxide were added and the resulting mixture stirred for about 22 hours. The reaction mixture was filtered and the filtrate concentrated in vacuo. The resulting concentrate was dissolved in chloroform and the chloroform solution chromatographed over 150 g. of florisil using chloroform containing increasing amounts (1–2%) of methanol as the eluant. Fractions shown by thin-layer chromatography to contain trans-dl-1-n-propyl-3-ethoxycarbonyl-6-oxodecahydroquinoline formed in the above reaction were combined and the solvent removed from the combined extracts to yield 3.48 g. of the 6-oxo compound as a residue. The 6-oxo compound was dissolved in 100 ml. of toluene containing an added 25 ml. of the dimethylacetal of dimethylformamide. The resulting mixture was heated to refluxing temperature under a nitrogen atmosphere for 44 hours and was then allowed to remain at room temperature for an additional 4 days. Volatile constituents were removed by evaporation in vacuo and the residue, comprising trans-dl-1-n-propyl-3-ethoxycarbonyl-6-oxo-7-(dimethylaminomethylene)decahydroquinoline formed in the above reaction, was purified by chromatographing a chloroform solution of the compound over florisil using chloroform containing increasing amounts (2–5%) of methanol as the eluant. Fractions shown by TLC to contain the desired 7-dimethylaminomethylene compound were combined and the solvent evaporated therefrom in vacuo.

The potassium salt of glycine was prepared by reacting 280 mg. of potassium hydroxide with 370 mg. of glycine in 50 ml. of anhydrous ethanol. 1.3 g. of trans-dl-1-n-propyl-3-ethoxycarbonyl-6-oxo-7-(dimethylaminomethylene)decahydroquinoline were added and the resulting mixture heated under a nitrogen atmosphere to reflux temperature for about 3 hours. The reaction mixture was cooled and the volatile constituents removed by evaporation in vacuo. 50 ml. of acetic anhydride were added to this residue and the resulting mixture heated to reflux temperature under a nitrogen atmosphere for about 45 minutes thus cyclizing, decarboxylating and acetylating all in one step. Again, the reaction mixture was cooled and the volatile constituents removed by evaporation. In this instance, the residue was next diluted with aqueous sodium bicarbonate and the resulting alkaline aqueous layer extracted with chloroform. The chloroform extract was separated and the separated extract washed with saturated aqueous sodium bicarbonate and then dried. Evaporation of the chloroform yielded a residue which was chromatographed over 35 g. of florisil using chloroform containing increasing amounts (0–1%) of methanol as the eluant. Fractions shown by TLC to contain the desired trans-dl-2-acetyl-5-n-propyl-7-ethoxycarbonyl-4,4a,5,6,7,8,8a,9-octahydropyrrolo[3,4-g]quinoline formed in the above reaction were combined. The solvent was removed from the combined fractions by evaporation and the resulting residue was dissolved in ether. This ether solution was treated with an excess of maleic acid, also in ether. The resulting precipitate comprising the maleate salt of trans-dl-2-acetyl-5-n-propyl-7-ethoxycarbonyl-4,4a,5,6,7,8,8a,9-octahydropyrrolo[3,4-g]quinoline melted at 179°–180° C. after crystallization from a methanol-ether solvent mixture; yield=280 mg.

Analysis Calculated: C, 61.59; H, 7.19; N, 6.25; Found: C, 61.32; H, 6.97; N, 6.53.

690 mg. of trans-dl-2-acetyl-5-n-propyl-7-ethoxycarbonyl-4,4a,5,6,7,8,8a,9-octahydropyrrolo[3,4-g]quinoline maleate were dissolved in ethanol and this solution added to a solution containing an excess of sodium ethylate in ethanol. The reaction mixture was stirred for ½ hour after which time it was diluted with water and the aqueous mixture extracted with chloroform. The chloroform extract was separated, washed with saturated aqueous sodium chloride and then dried. Evaporation of the chloroform yielded trans-dl-5-n-propyl-7-ethoxycarbonyl-4,4a,5,6,7,8,8a,9-octahydropyrrolo[3,4-g]quinoline formed in the above reaction. The free base melted at 163°–4° C. after recrystallization from ethanol.

Analysis calculated: C, 70.31; H, 9.02; N, 9.65 Found: C, 70.22; H, 8.91; N, 9.94.

About ½ gram of trans-dl-5-n-propyl-7-ethoxycarbonyl-4,4a,5,6,7,8,8a,9-octahydropyrrolo[3,4-g]quinoline were dissolved in 75 ml. of tetrahydrofuran. 1 g. of lithium aluminumhydride was added thereto in small portions. After all of the lithium aluminumhydride had been added, the reaction mixture was stirred for another 2.25 hours after which time the excess lithium aluminumhydride was decomposed by the addition of ethyl acetate and any organometallic salts present decomposed by the addition of 10% aqueous sodium hydroxide. The resulting mixture was diluted with water and the aqueous layer extracted several times with chloroform. The chloroform extracts were separated and combined and the combined extracts washed with saturated aqueous sodium chloride and then dried. Evaporation of the solvent yielded as a residue, trans-dl-5-n-propyl-7-hydroxymethyl-4,4a,5,6,7,8,8a,9-octahydropyrrolo[3,4-g]quinoline, which melted at 178°–180° C. after recrystallization from a ethyl acetate/ether solvent mixture.

Analysis calculated: C, 72.54; H, 9.74; N, 11.28 Found: C, 72.30; H, 9.73; N, 11.05.

About 0.4 g. of trans-dl-5-n-propyl-7-hydroxymethyl-4,4a,5,6,7,8,8a,9-octahydropyrrolo[3,4-g]quinoline were dissolved in 25 ml. of pyridine. 0.5 ml. of methanesulfonyl chloride were added and the resulting mixture stirred for 0.75 hours at room temperature. The reaction mixture was diluted with water and sufficient 14 N aqueous ammonium hydroxide added to make the reaction mixture basic. The aqueous mixture was extracted several times with ethyl acetate. The ethyl acetate extracts were combined and the combined extracts washed first with water and then with saturated aqueous ammonium chloride and were then dried. The residue obtained by evaporation of the solvent was chromatographed over 30 g. of florisil and the chromatogram develop with chloroform containing increasing quantities (2–4%) of methanol as the eluant. Fractions shown by thin-layer chromatography to contain the desired methanesulfonyl ester were combined and the solvent removed therefrom in vacuo. The resulting residue, trans-dl-5-n-propyl-7-mesyloxymethyl-4,4a,5,6,7,8,8a,9-octahydropyrrolo[3,4-g]quinoline was crystallized from ethanol; m.p.=150° C. with decomposition.

The mesylate ester thus prepared can be reacted with the sodium salt of methylmercaptan to yield trans-dl-5-n-propyl-7-methylmercaptomethyl-4,4a,5,6,7,8,8a,9-octahydropyrrolo[3,4-g]quinoline.

As evidence of the utility of the compounds of this invention, it has been found that they affect turning behavior in rats in a test procedure designed to uncover compounds useful for the treatment of Parkinsonism utilizing 6-hydroxydopamine-lesioned rats. In this test, nigro-neostriatal-lesioned rats are employed, as prepared by the procedure of Ungerstedt and Arbuthnott, *Brain Res*, 24, 485 (1970). A compound having dopamine agonist activity causes the rats to turn in circles contralateral to the side of the lesion. After a latency period, which varies from compound to compound, the number of turns is counted over a 15-minute period.

Results obtained from testing representative compounds of this invention in the rat turning test are set forth in Table 1 below. The compounds were dissolved in water and the aqueous solution injected into the rat by the intraperitoneal route at a dose level of 1 mg/kg. In the table, column 1 gives the name of the compound, column 2, percent of test animals exhibiting turning behavior, and column 3, average number of turns observed in first 15 minutes after end of latency period.

TABLE 1

| Name of Compound | % of Rats Exhibiting Turning Behavior | Average Number of Turns/rat |
|---|---|---|
| trans-dl-5-n-Propyl-4,4a,5,6-7,8,8a,9-octahydro-2H-pyrrolo[3,4-g]quinoline maleate | 100 | 169 |
| trans-dl-5-Methyl-4,4a,5,6,7,8,-8a,9-octahydro-2H-pyrrolo[3,4-g]quinoline maleate | 33 | 20 |
| trans-dl-5-n-Propyl-7-hydroxymethyl-4,4a,5,6,7,8,8a,9-octahydro-2H-pyrrolo[3,4-g]quinoline | 100 | 109 |

The compounds of this invention are also useful as prolactin inhibitors and as such they can be employed in the treatment of inappropriate lactation such as postpartum lactation and galactorrhea. As evidence of their utility in the treatment of diseases such as those in which it is desirable to reduce the prolactin level, the compounds of this invention have been shown to inhibit prolactin according to the following procedure.

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the test drug. The purpose of the reserpine was to keep prolactin levels uniformly elevated. The compounds under test were dissolved in 10 percent ethanol, and were injected intraperitoneally at doses of 0.5 and 5 mg/kg. Each compound was administered at each dose level to a group of 10 rats, and a control group of 10 intact males received an equivalent amount of 10 percent ethanol. One hour after treatment, all rats were killed by decapitation, and 150 µl aliquots of serum were assayed for prolactine.

The difference between the prolactin level of the treated rats and prolactin level of the control rats, divided by the prolactin level of the control rats gives the percent inhibition of prolactin secretion attributable to the compounds of this invention. These inhibition percentages are given in Table 2 below. In the table, column 1 gives the name of the compound; and columns 2 and 3, the percent prolactin inhibition at the 0.5 and 5 mg/kg dose levels.

TABLE 2

| Name of Compound | Percent Prolactin Inhibition at Given Dose | |
|---|---|---|
| | 0.5 mg/kg | 5 mg/kg |
| trans-dl-5-n-Propyl-4,4a,5,6,7,8,8a,9-octahydro-2H-pyrrolo[3,4-g]quinoline maleate | — | 95 |
| trans-dl-5-Methyl-4,4a,5,6,7,8,8a,9-octahydro-2H-pyrrolo[3,4-g]quinoline maleate | 23 | 90 |

In using the compounds of this invention to inhibit prolactin secretion or to treat Parkinson's syndrome or for other pharmacologic action, a compound according to Formula I above in which $R^2$ is $C_1$–$C_3$ alkyl or allyl and $R^1$ is H or $C_1$–$C_3$ alkyl, or a salt thereof with a pharmaceutically-acceptable acid, is administered to a subject suffering from Parkinsonism or in need of having his prolactin level reduced in an effective amount to treat Parkinsonism or to reduce prolactin. Oral administration is preferred. If parenteral administration is used, the injection is preferably by the subcutaneous route using an appropriate pharmaceutical formuation. Other modes of parenteral administration such as intraperitoneal, intramuscular, or intravenous routes are equally effective. In particular, with intravenous or intramuscular administration, a water soluble pharmaceutically-acceptable salt is employed. For oral administration, the compound either as the free base or in the form of a salt thereof can also be mixed with standard pharmaceutical excipients and loaded into empty telescoping gelatin capsules or pressed into tablets. For oral administration, the compound either as the free base or in the form of a salt thereof, can also be mixed with standard pharmaceutical excipients and loaded into empty telescoping gelatin capsules or pressed into tablets. The oral dosage range is from about 0.01 to 10 mg. to 10 mg./kg. of mammalian weight and the parenteral dose range from about 0.0025 to 2.5 mg./kg. Intraperitoneal dosages of 10–30 mg./kg. of trans-dl-5-n-propyl-4,4a,5,6,7,8,8a,9-octahydro-pyrrolo[3,4-g]-quinoline dihydrochloride resulted in no deaths, but dosages of 100–300 mg./kg. were fatal, indicating an $LD_{50}$ in the range 30–100 mg./kg.

We claim:

1. A compound of the formula

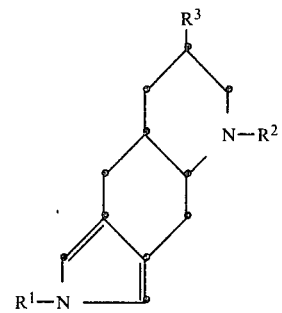

wherein $R^1$ is H, or $(C_1$–$C_3)$alkyl, $R^2$ is H, $C_1$–$C_3$ alkyl, allyl or benzyl and $R^3$ is $COO(C_1$–$C_3)$ alkyl, COOH, or $CH_2X$ wherein X is CN, $CONH_2$, $SCH_3$, $SO_2CH_3$, or $OCH_3$ or a pharmaceutically acceptable acid addition salt thereof.

2. A compound according to claim 1 in which $R^1$ is H or $(C_1$–$C_3)$alkyl, $R^2$ is $(C_1$–$C_3)$ alkyl or allyl and $R^3$ is $CH_2X$ wherein X is $SCH_3$, $OCH_3$, CN, $CONH_2$ or $SO_2CH_3$ or a pharmaceutically-acceptable acid addition salts thereof.

3. A compound according to claim 1 in which $R^1$ is H or $(C_1$–$C_3)$alkyl—CO, and $R^2$ is H or benzyl or an acid addition salt thereof.

4. A compound according to claim 1, said compound being trans-dl-2-acetyl-5n-propyl-7-ethoxycarbonyl-4,4a,5,6,7,8,8a,9-octahydropyrrolo[3,4-g]quinoline.

* * * * *